(12) United States Patent
Tomasetti et al.

(10) Patent No.: US 7,722,733 B2
(45) Date of Patent: May 25, 2010

(54) METHOD FOR STERILE CONNECTION OF TUBING

(75) Inventors: Eric Tomasetti, Jemeppe on Sambre (BE); Michel Joie, Ernage (BE)

(73) Assignee: Baxter International Inc., Deerfield, IL (US)

( * ) Notice: Subject to any disclaimer, the term of this patent is extended or adjusted under 35 U.S.C. 154(b) by 168 days.

(21) Appl. No.: 10/811,589

(22) Filed: Mar. 29, 2004

(65) Prior Publication Data

US 2005/0211373 A1  Sep. 29, 2005

(51) Int. Cl.
*B32B 15/00* (2006.01)

(52) U.S. Cl. ............... 156/156; 156/265; 156/242; 156/512; 156/56; 156/307.1; 156/272.2; 156/275.1; 156/272.4; 156/273.7

(58) Field of Classification Search ............. 156/272.2, 156/275.1, 272.4, 273.7
See application file for complete search history.

(56) References Cited

U.S. PATENT DOCUMENTS

| | | | |
|---|---|---|---|
| 3,063,890 A | 11/1962 | Saumsiegle |
| 3,542,712 A | 11/1970 | Gorton et al. |
| 3,645,939 A | 2/1972 | Gaylord et al. |
| 3,725,174 A | 4/1973 | Gaylord et al. |
| 3,734,819 A | 5/1973 | Knutson |
| 3,763,073 A | 10/1973 | Knutson |
| 3,767,633 A | 10/1973 | Dietrich |
| 3,956,230 A | 5/1976 | Gaylord |
| 4,004,586 A | 1/1977 | Christensen et al. |
| 4,029,850 A | 6/1977 | Ishii et al. |
| 4,037,020 A | 7/1977 | Ishii et al. |
| 4,046,728 A | 9/1977 | Harmuth |
| 4,071,494 A | 1/1978 | Gaylord |
| 4,089,726 A | 5/1978 | Ishii et al. |
| 4,126,504 A | 11/1978 | Wolinski et al. |
| 4,161,949 A | 7/1979 | Thanawalla |
| 4,209,013 A | 6/1980 | Alexander et al. |
| 4,210,567 A | 7/1980 | Kosters |
| 4,230,774 A | 10/1980 | Watts et al. |
| 4,265,280 A | 5/1981 | Ammann et al. |
| 4,316,832 A | 2/1982 | Walkden |
| 4,322,516 A | 3/1982 | Wiest et al. |
| 4,327,726 A | 5/1982 | Kwong et al. |
| 4,369,779 A | 1/1983 | Spencer |

(Continued)

FOREIGN PATENT DOCUMENTS

CA  1 205 783  6/1986

(Continued)

OTHER PUBLICATIONS

PCT International Preliminary Report of Patentability for PCT/US2005/006630 dated Oct. 12, 2006.

(Continued)

*Primary Examiner*—Philip C Tucker
*Assistant Examiner*—Kimberly K McClelland
(74) *Attorney, Agent, or Firm*—K&L Gates LLP

(57) ABSTRACT

A method for sterile connection of tubing includes welding the tubing sections together using an efficient laser. The ends of the tubing sections are brought together prior to the initiation of welding, facilitating isolation of interior passage of the tubing sections. The method can be carried out by an apparatus which is relatively inexpensive and compact.

7 Claims, 12 Drawing Sheets

U.S. PATENT DOCUMENTS

| | | |
|---|---|---|
| 4,410,026 A | 10/1983 | Boggs et al. |
| 4,412,835 A | 11/1983 | Spencer |
| 4,417,753 A | 11/1983 | Bacehowski et al. |
| 4,439,192 A | 3/1984 | Leurink |
| 4,443,215 A | 4/1984 | Smith |
| 4,488,961 A | 12/1984 | Spencer |
| 4,495,312 A | 1/1985 | Hata et al. |
| 4,496,362 A | 1/1985 | Leurink |
| 4,507,119 A | 3/1985 | Spencer |
| 4,516,971 A | 5/1985 | Spencer |
| 4,516,977 A | 5/1985 | Herbert |
| 4,525,234 A | 6/1985 | Herold et al. |
| 4,587,289 A | 5/1986 | Comert |
| 4,588,402 A | 5/1986 | Igari et al. |
| 4,601,948 A | 7/1986 | Lancaster et al. |
| 4,610,469 A | 9/1986 | Wolff-Mooij |
| 4,610,670 A | 9/1986 | Spencer |
| 4,619,642 A | 10/1986 | Spencer |
| 4,650,220 A | 3/1987 | Grabowski |
| 4,663,032 A | 5/1987 | Loos et al. |
| 4,664,658 A | 5/1987 | Sawada et al. |
| 4,668,217 A | 5/1987 | Isono |
| 4,673,400 A | 6/1987 | Martin |
| 4,687,474 A | 8/1987 | Takanashi |
| 4,707,389 A | 11/1987 | Ward |
| 4,720,524 A | 1/1988 | Ohmae et al. |
| 4,723,947 A | 2/1988 | Konopka |
| 4,725,641 A | 2/1988 | Comert et al. |
| 4,726,960 A | 2/1988 | Sawada et al. |
| 4,737,214 A | 4/1988 | Leurink et al. |
| 4,739,012 A | 4/1988 | Hagman |
| 4,740,017 A | 4/1988 | Grabowski |
| 4,753,697 A | 6/1988 | Spencer et al. |
| 4,770,735 A | 9/1988 | Spencer et al. |
| 4,771,106 A | 9/1988 | Ohmae et al. |
| 4,784,409 A | 11/1988 | Piechowiak |
| 4,786,286 A | 11/1988 | Cerny et al. |
| 4,793,880 A * | 12/1988 | Shaposka et al. ............. 156/158 |
| 4,827,099 A | 5/1989 | Krebs et al. |
| 4,828,557 A | 5/1989 | Persidsky |
| 4,832,773 A * | 5/1989 | Shaposka et al. ............. 156/158 |
| 4,848,801 A | 7/1989 | Grabowski |
| 4,864,101 A | 9/1989 | Spencer et al. |
| 4,865,902 A | 9/1989 | Golike et al. |
| 4,880,873 A | 11/1989 | Sagane |
| 4,897,138 A | 1/1990 | Spencer et al. |
| 4,900,771 A | 2/1990 | Gerace et al. |
| 4,913,756 A | 4/1990 | Spencer et al. |
| 4,927,184 A | 5/1990 | Bourjot et al. |
| 4,933,036 A | 6/1990 | Spencer et al. |
| 4,946,455 A | 8/1990 | Rosen |
| 4,948,062 A * | 8/1990 | Mahar et al. ............. 242/538.2 |
| 4,948,643 A | 8/1990 | Mueller |
| 4,997,430 A | 3/1991 | Heiden et al. |
| 5,026,019 A | 6/1991 | Biekart et al. |
| 5,037,395 A | 8/1991 | Spencer |
| 5,039,768 A | 8/1991 | Gerace et al. |
| 5,061,451 A | 10/1991 | Ganshirt et al. |
| 5,088,994 A | 2/1992 | Porat et al. |
| 5,135,600 A | 8/1992 | Ishida |
| 5,141,592 A | 8/1992 | Shaposka et al. |
| 5,156,701 A | 10/1992 | Spencer et al. |
| 5,158,630 A | 10/1992 | Spencer et al. |
| 5,166,269 A | 11/1992 | Wietsma et al. |
| 5,179,496 A | 1/1993 | Mimura |
| 5,188,697 A | 2/1993 | Lueghamer et al. |
| 5,209,800 A | 5/1993 | Spencer et al. |
| 5,224,937 A | 7/1993 | Heiden et al. |
| 5,244,522 A | 9/1993 | Spencer et al. |
| 5,248,359 A | 9/1993 | Shaposka et al. |
| 5,248,562 A | 9/1993 | Palermo et al. |
| 5,250,607 A | 10/1993 | Comert et al. |
| 5,254,825 A | 10/1993 | Schippers |
| 5,256,229 A | 10/1993 | Spencer |
| 5,256,845 A | 10/1993 | Schippers |
| 5,272,304 A | 12/1993 | Been et al. |
| 5,274,035 A | 12/1993 | Chundury |
| 5,279,685 A | 1/1994 | Ivansons et al. |
| 5,324,233 A | 6/1994 | Owensby et al. |
| 5,336,351 A | 8/1994 | Meyers |
| 5,342,345 A | 8/1994 | Spencer |
| 5,345,070 A * | 9/1994 | Hlavinka et al. ............. 219/769 |
| 5,356,709 A | 10/1994 | Woo et al. |
| 5,367,010 A | 11/1994 | Gervase et al. |
| 5,368,586 A | 11/1994 | Heiden et al. |
| 5,371,767 A | 12/1994 | Pirl |
| 5,378,313 A * | 1/1995 | Pace ............................ 216/20 |
| 5,385,979 A | 1/1995 | Osawa et al. |
| D355,848 S | 2/1995 | Spencer et al. |
| 5,391,610 A | 2/1995 | Comert et al. |
| 5,397,425 A | 3/1995 | Spencer et al. |
| 5,407,742 A | 4/1995 | Tayss et al. |
| 5,410,131 A | 4/1995 | Brunet et al. |
| D357,926 S | 5/1995 | Spencer et al. |
| 5,439,454 A | 8/1995 | Lo et al. |
| 5,460,625 A | 10/1995 | Johnson |
| 5,464,496 A | 11/1995 | Wilson et al. |
| 5,476,718 A | 12/1995 | Ichizuka et al. |
| 5,484,375 A | 1/1996 | Owensby et al. |
| 5,486,210 A | 1/1996 | Kerr et al. |
| 5,492,963 A | 2/1996 | Ozawa et al. |
| 5,496,291 A | 3/1996 | Spencer |
| 5,518,575 A | 5/1996 | Watanabe |
| 5,520,218 A | 5/1996 | Hlavinka et al. |
| 5,525,186 A | 6/1996 | Spencer et al. |
| 5,534,591 A | 7/1996 | Ozawa et al. |
| 5,554,253 A | 9/1996 | Watanabe |
| 5,562,882 A | 10/1996 | Smith et al. |
| 5,601,889 A | 2/1997 | Chundury et al. |
| 5,620,738 A | 4/1997 | Fan et al. |
| 5,632,852 A | 5/1997 | Ivansons et al. |
| 5,656,345 A | 8/1997 | Strand et al. |
| 5,674,333 A * | 10/1997 | Spencer ...................... 156/64 |
| 5,686,527 A | 11/1997 | Laurin et al. |
| 5,733,268 A | 3/1998 | Spencer |
| 5,744,094 A * | 4/1998 | Castberg et al. ............... 422/24 |
| 5,749,414 A | 5/1998 | Damsohn et al. |
| 5,802,689 A | 9/1998 | Sano |
| 5,810,792 A | 9/1998 | Fangrow et al. |
| 5,821,293 A | 10/1998 | Roesch et al. |
| 5,824,724 A | 10/1998 | Roesch et al. |
| 5,849,843 A | 12/1998 | Laurin et al. |
| 5,854,347 A | 12/1998 | Laurin et al. |
| 5,855,731 A | 1/1999 | Spencer |
| 5,871,612 A | 2/1999 | Spencer |
| 5,877,236 A | 3/1999 | Roesch et al. |
| 5,879,318 A | 3/1999 | Heiden et al. |
| 5,888,328 A | 3/1999 | Miripol et al. |
| 5,919,173 A | 7/1999 | Spencer |
| 5,921,587 A | 7/1999 | Lueghamer |
| 5,922,798 A | 7/1999 | Roesch et al. |
| 5,928,216 A | 7/1999 | Spencer |
| 5,935,847 A | 8/1999 | Smith et al. |
| 5,964,261 A | 10/1999 | Neuenfeldt et al. |
| 5,965,086 A | 10/1999 | Rose et al. |
| 5,968,380 A | 10/1999 | Hayashi |
| 5,993,949 A | 11/1999 | Smith et al. |
| 5,998,019 A | 12/1999 | Rosenbaum et al. |
| 6,004,311 A | 12/1999 | Heilmann et al. |
| 6,004,417 A | 12/1999 | Roesch et al. |
| 6,020,574 A | 2/2000 | Ivansons |
| 6,022,344 A | 2/2000 | Meijer |
| 6,024,220 A | 2/2000 | Smith et al. |
| 6,026,882 A | 2/2000 | Yamada et al. |

| | | | |
|---|---|---|---|
| 6,027,489 A | 2/2000 | Galato | |
| 6,071,690 A | 6/2000 | Spencer | |
| 6,083,584 A | 7/2000 | Smith et al. | |
| 6,094,969 A | 8/2000 | Loos et al. | |
| 6,132,833 A | 10/2000 | Spencer | |
| 6,140,657 A | 10/2000 | Wakalopulos et al. | |
| 6,149,997 A | 11/2000 | Patel et al. | |
| 6,168,862 B1 | 1/2001 | Rosenbaum et al. | |
| 6,177,652 B1 | 1/2001 | Ivansons | |
| 6,201,211 B1 | 3/2001 | Emmelmann | |
| 6,225,404 B1 | 5/2001 | Sorensen et al. | |
| 6,251,202 B1 | 6/2001 | Murphy | |
| 6,261,655 B1 | 7/2001 | Rosenbaum et al. | |
| 6,270,599 B1 | 8/2001 | Wood | |
| 6,293,594 B1 | 9/2001 | Safarevich et al. | |
| 6,296,730 B1 | 10/2001 | Williams et al. | |
| 6,297,046 B1 | 10/2001 | Smith et al. | |
| 6,299,596 B1 | 10/2001 | Ding | |
| 6,302,151 B1 | 10/2001 | Maitay | |
| 6,308,882 B1 | 10/2001 | Shuster et al. | |
| 6,333,122 B1 | 12/2001 | Furukawa et al. | |
| 6,341,637 B1 | 1/2002 | Yamada et al. | |
| 6,368,315 B1 | 4/2002 | Gillis et al. | |
| 6,399,704 B1 | 6/2002 | Laurin et al. | |
| 6,465,068 B1 | 10/2002 | Patel et al. | |
| 6,596,122 B1 | 7/2003 | Savitski et al. | |
| 6,860,960 B1 * | 3/2005 | Flanagan | 156/272.8 |
| 2002/0006353 A1 | 1/2002 | Bilstad et al. | |
| 2002/0018731 A1 | 2/2002 | Bilstad et al. | |
| 2002/0100540 A1 | 8/2002 | Savitski et al. | |
| 2003/0141009 A1 | 7/2003 | Landherr et al. | |
| 2003/0141634 A1 | 7/2003 | Shang et al. | |
| 2003/0143352 A1 * | 7/2003 | Yang et al. | 428/36.9 |
| 2003/0226631 A1 * | 12/2003 | Sterud et al. | 156/64 |
| 2004/0059063 A1 | 3/2004 | Yang et al. | |

FOREIGN PATENT DOCUMENTS

| | | |
|---|---|---|
| CN | 1052131 | 6/1991 |
| DE | 3 734 170 A1 | 4/1989 |
| EP | 0 307 546 A1 | 3/1989 |
| EP | 0 406 485 A1 | 1/1991 |
| EP | 0 418 772 A2 | 3/1991 |
| EP | 0 515 811 | 12/1992 |
| EP | 0 515 811 A2 | 12/1992 |
| EP | 0 583 582 A1 | 2/1994 |
| EP | 0 508 251 B1 | 8/1995 |
| EP | 0 689 846 A1 | 1/1996 |
| EP | 0 619 175 A3 | 3/1996 |
| EP | 0 723 851 A2 | 7/1996 |
| EP | 0 725 134 A2 | 8/1996 |
| EP | 0 564 231 A1 | 5/1997 |
| EP | 0 778 123 | 6/1997 |
| EP | 0 778 123 A2 | 6/1997 |
| EP | 0 813 274 A1 | 12/1997 |
| EP | 0 903 214 A1 | 3/1999 |
| EP | 0 931 563 A3 | 4/2000 |
| EP | 1 064 960 A2 | 1/2001 |
| EP | 1 303 387 B1 | 6/2006 |
| JP | 46042639 | 12/1971 |
| JP | 72044977 | 11/1972 |
| JP | 57-150533 | 9/1982 |
| JP | 62-244614 | 10/1987 |
| JP | 63-126709 | 5/1988 |
| JP | 1-210486 | 8/1989 |
| JP | 2-113052 | 4/1990 |
| JP | 2-269753 | 11/1990 |
| JP | 3-120042 | 5/1991 |
| JP | 3-177682 | 8/1991 |
| JP | 4-208419 | 7/1992 |
| JP | 5-42640 | 2/1993 |
| JP | 5-124146 | 5/1993 |
| JP | HEI 6-91010 | 4/1994 |
| JP | HEI 6-91011 | 4/1994 |
| JP | HEI 6-233817 | 8/1994 |
| JP | 08-003526 | 1/1996 |
| JP | 08-003527 | 1/1996 |
| JP | 08-174676 A | 7/1996 |
| JP | 8-295862 | 11/1996 |
| JP | 2000-126288 A | 5/2000 |
| JP | 2000-170967 A | 6/2000 |
| JP | 2000-301592 A | 10/2000 |
| JP | 2000-344852 A | 12/2000 |
| JP | 2002-146303 A | 5/2002 |
| NL | 8101191 | 10/1982 |
| WO | 82/02528 | 8/1982 |
| WO | WO 82/02528 A1 | 8/1982 |
| WO | 93/15908 | 8/1993 |
| WO | 98/36902 A1 | 8/1998 |
| WO | 99/24242 A1 | 5/1999 |
| WO | 00/05316 A1 | 2/2000 |
| WO | WO 00/62820 | 10/2000 |
| WO | 01/46332 A1 | 6/2001 |
| WO | 01/60586 A1 | 8/2001 |
| WO | 01/62314 A2 | 8/2001 |
| WO | 01/66662 A2 | 9/2001 |
| WO | WO 02/066098 A1 | 8/2002 |
| WO | 2005/102671 A1 | 3/2005 |

OTHER PUBLICATIONS

Web page http://www.cellrobtics.com/perslasette.html printed on Aug. 3, 2001.
Web page http://www.laserweld.com/laser-welding.html printed on Mar. 21, 2001.
Web page http://www.coherentic.com/html/about.html printed on Mar. 21, 2001.
Web page http://www.dencotcd.com.
LaseRevolution, Inc. web page printed Mar. 21, 2001. (No current web site available).
Joining Technologies LLC web page, "Electron Beam Welding", printed Mar. 20, 2001. http://www.joiningtech.com/eb.html.
Ebeam web page printed Mar. 20, 2001. (No current web site address available).
Dimetrics,Inc. web page printed Mar. 20, 2001. http://www.liburdi.comiliburdidimetrics/index.php.
MPW web page printed Mar. 20, 2001. http://www.mpwaustralia.com (address to specific printed web page is currently unavailable).
Fresenius HemoCare, Inc. web page printed Jun. 6, 2002. http://www.freseniushc.comiproduct/bloodbanking.html (page has been updated).
Industrial Microphotonics Company web page printed'Mar. 21, 2001. www.imclaser.com address redirects to NorthrupGrumman webpage, http://www.st.northrupgrumman.com/ceolaser.
Joining Technologies web page, "Weld Joint Design", printed Mar. 21, 2001. http://wwwjoiningtech.com (address to specific printed web page is currently unavailable).
Electrox—Manufacturing Solutions web page printed Mar. 21, 2001. http://www.electrox.com (address to specific printed web page is currently unavailable).
TWI Technology web page printed.Mar. 21, 2001. http://www.twi.co.uk/j32k/unprotected/band 1/tfindex.html (address to specific printed web is currently unavailable).
Joining Technologies, "Laser Beam Welding", printed Mar. 21, 2001. http://www.joiningtech.com/laser.html.
US 5,693,387, 12/1997, Rosenbaum et al. (withdrawn)

* cited by examiner

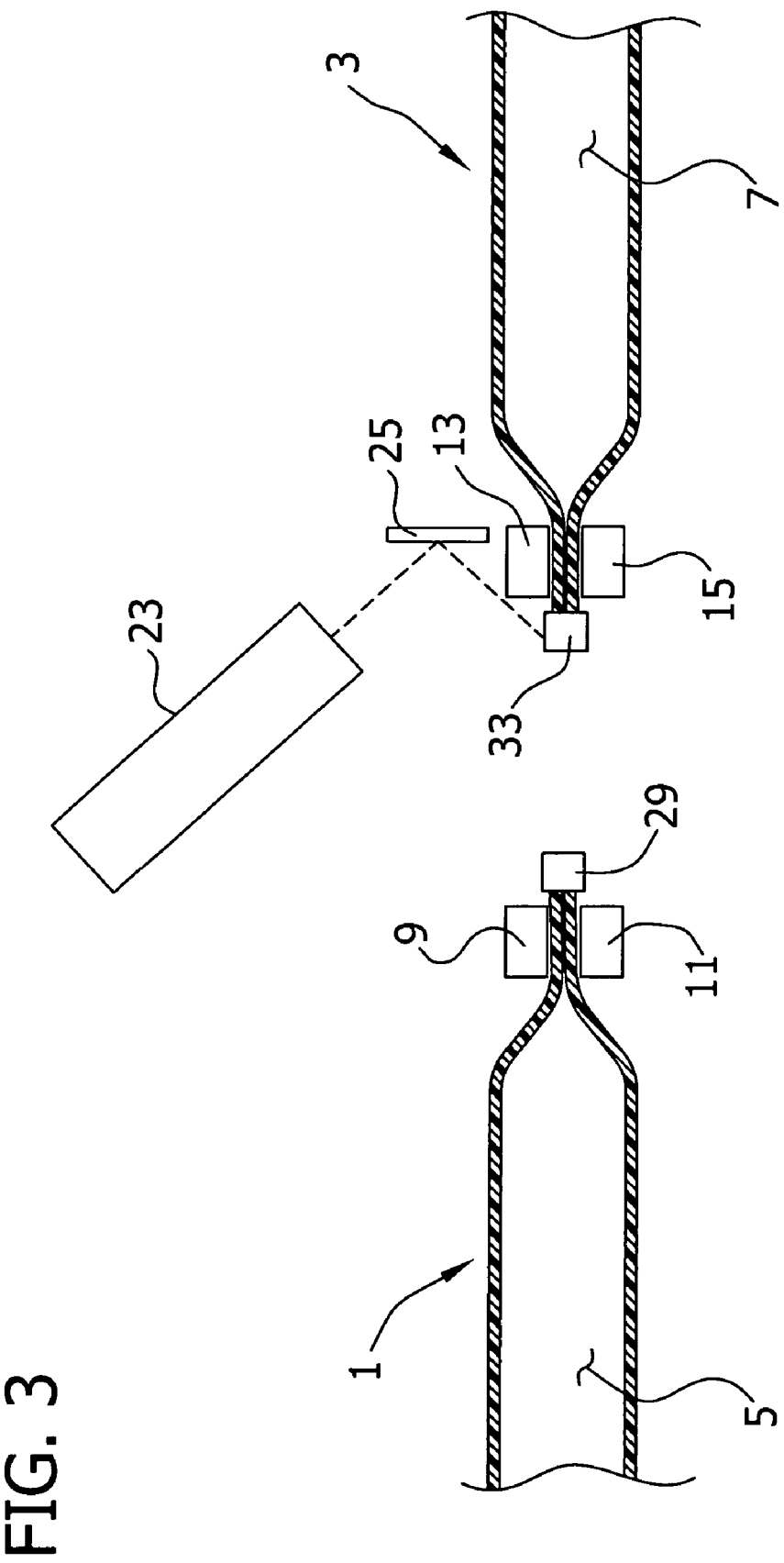

METHOD FOR STERILE CONNECTION OF TUBING

BACKGROUND OF THE INVENTION

This invention relates generally to the connection of flexible polymeric tubing sections, and more particularly to methods and apparatus for connecting such tubing sections so as to maintain a sterile condition in an interior passage of the tubing.

Medical containers with tubing are used for various medical procedures such as kidney dialysis, intravenous delivery of therapeutic fluids, delivery of nutritional fluids; delivery of blood, blood components, and blood substitutes. Fluid containers and tubing are also widely used in other industries such as the food industry and the chemical industries.

One example in the medical context is when two flowable medical products (e.g., liquids and mixtures of liquids and solids) need to be delivered to the patient at the same time, but the two products cannot be sterilized in the same way.

It is possible to manufacture both products (even as a mixture) in an aseptic environment. This is expensive and may not lead to a level of sterilization in the final product which is superior to making and packaging the products in a nonsterile environment and subsequently sterilizing both the products and the package. Another option is to package the products separately and connect them at the time of use. However, this requires a sterile connection of the packages, and more specifically a sterile connection of tubes connected to the packages.

As another example requiring sterile connection of tubing, flexible medical tubing is used in systems for treating renal disease. The balance of water, minerals and the excretion of daily metabolic load is no longer possible in renal failure. During renal failure, toxic end products of nitrogen metabolism (urea, creatinine, uric acid and others) can accumulate in blood and tissues. This condition is commonly treated with dialysis.

Dialysis removes waste toxins and excess water from the body that would otherwise have been removed by normal functioning kidneys. Dialysis treatment for replacement of kidney functions is critical to many people because the treatment is lifesaving. One who has failed kidneys could not continue to live without replacing at least the filtration functions of the kidneys. Hemodialysis and peritoneal dialysis are two types of dialysis therapies commonly used to treat loss of kidney function.

In general, hemodialysis treatment removes waste, toxins, and excess water from the patient's blood. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, waste, toxins, and excess water are removed from the patient's blood and the blood is infused back into the patient. Many tubes are used in the process that must be connected or disconnected. Peritoneal dialysis typically utilizes a dialysis solution, or dialysate, which is infused into a patient's peritoneal cavity. Waste, toxins and excess water pass from the patient's bloodstream through his/her peritoneal membrane and into the dialysate. The transfer of waste, toxins and water from the bloodstream into the dialysate occurs due to diffusion and osmosis, i.e., there is an osmotic gradient across the membrane. The spent dialysate is drained from the patient's peritoneal cavity to remove the waste, toxins and water from the patient. After the spent dialysis is drained, it is replaced with a fresh dialysate solution.

In peritoneal dialysis, a patient has a catheter implanted in his/her peritoneal cavity with an end protruding from the patient. The protruding end of the catheter terminates with a section of tubing known as a transfer set. The transfer set is typically made from a silicone material and must be periodically replaced. The transfer set is provided to connect the patient to dialysate fluid bags or discharge bags. The transfer set typically has a spike that connects to an access port positioned in a tube associated with the drain bag or dialysate solution bag (dialysate set). In general, the patient manually stabs the port with the spike to connect the transfer set to the dialysate set. The patient connects the tube in the transfer set to a drain to allow spent dialysate fluid to drain from the peritoneal cavity. Next, the patient is connected to a bag of fresh dialysate and manually infuses the fresh dialysate through the catheter and into the patient's peritoneal cavity. When the patient completes treatment, the port is pulled off the spike and a cap is placed on a spike until the patient is ready for the next treatment. When the patient disconnects the catheter from the fresh dialysate bag, the dialysate dwells within the peritoneal cavity to draw waste, toxins and excess water from the patient's bloodstream to the dialysate solution. After the dwell period, the patient repeats the manual dialysis procedure and drains the spent dialysate from the peritoneal cavity.

Accordingly, during dialysis treatments such as those described above, the patient is required to connect and disconnect the catheter and transfer set from the fill or drain line (or tube) a number of times. Some devices are available today to assist the patient during the process when using specialized sterilization equipment. However, by and large, these connections and disconnections are performed manually.

One such device incorporates a heated wafer or hot knife that physically contacts the tubing to cut it by melting the tube and joining two tubes together or melt-sealing the tube ends. Typically, heated wafer applications involve a "melt and wipe" process. In peritoneal dialysis, for example, a patient must drain spent dialysate or replenish his/her peritoneal cavity with fresh dialysate. To this end, the patient must connect the transfer set tubing to a tube extending from either a drain bag or a bag containing fresh dialysate. In one "melt and wipe" process, the transfer set tubing is bent in a U or V-shape to fit into a first U or V-shaped tube holder. Similarly, the bag-side tube is bent in a U or V-shape to fit into a second U or V-shaped tube holder adjacent the first tube holder. A heated wafer moves across the space between the two tube holders and physically contacts the tubing at the bend junction of the U-shape or V-shape. As the heated wafer contacts the tubing, it melts the tube at the bend junction of the U-shape or V-shape. The wafer then wipes the melted tubing material and removes the material from the area between the first and second tube holders. The two holders are brought together and two connections are made. In the first connection, the transfer set tubing is connected to the bag-side tube and the dialysis process is ready to begin. In the second connection, the wasted tube material from the transfer set tubing and the bag-side tube is connected together and discarded.

In order to disconnect the patient from the bag, hot knives are used to cut the tube. An example of a known disconnecting process with the hot knives involves two tubes that are placed side by side across two tube holders. One of the tubes is a short tube having two sealed ends. Generally, the tube holders include a ridge at one end of the tube holder to flatten a portion of the tube to stop fluid flow. The hot knife severs each tube into two pieces. After the hot knife cuts the tube, one of the tube holders moves in relation to the other tube holder. The tubing is "swapped," realigned with one of the cut portions of the short tube, and connected to it—thus, a disconnection is made between the patient and the bag.

These devices have a relatively low level of reliability due to the inconsistency in melting and cutting processes. The inconsistency of operation can result in imperfect seals, leading to leaks, and bacterial infiltration which may lead to infection or peritonitis. Moreover, both connections require the heated ends of the tube to be uncovered and exposed to the surrounding environment before the connection is made. This can lead to contamination of the tube ends, and ultimately of the interior of the tubes, even if the device works perfectly.

The interior passages of the tubing sections are initially sterile, but cutting the tubing sections so that connections of adjacent sections can be made exposes the interior passages of the tubing sections to the surrounding environment, allowing them to potentially become contaminated with airborne contaminants, e.g., bacteria. Moreover, if the tubing sections are open, solid material from the unsterile exteriors of the tubing sections could enter the tubing sections. In the applications just described, it is impractical to engage in a resterilization procedure every time a new connection of tubing sections is made. Accordingly, it is recognized that the interior passages of the tubing sections need to be isolated while the tubing sections are being connected together.

In order to avoid exposure of the interior passage of each tubing section, it is known to clamp the end portion of the tubing section shut before an end portion of the tubing section is cut. However, axially facing surfaces at the very ends of the tubes are exposed to their surroundings. In some systems a hot blade or other heated surface is brought into contact with the exposed ends of the tubing sections to bring them up to melting temperature. The ends of the two tubing sections are then brought together so that the melted ends fuse, connecting the tubing sections together. The clamps collapsing the respective end portions of the tubing sections are released and the tubing sections open, defining a continuous, sealed interior passage through the connected tubing sections. In time, however, the heated blade or other surface becomes fouled with the plastic material of the tube, requiring cleaning to maintain operability. Moreover, it is necessary to apply enough energy in heating the ends so that they do not drop below a temperature at which fusion will occur before the two ends of the tubing sections are brought together.

Other tube connection systems have applied heat to the ends of the tubing sections without requiring direct contact of heating elements with the tubing sections. Examples of these types of systems are disclosed in the following patent applications, the disclosures of which are incorporated herein by reference: Apparatus and Method for Connecting and Disconnecting Flexible Tubing, U.S. application Ser. No. 10/061,835, filed Jan. 31, 2002; Coupler Member for Joining Dissimilar Materials, U.S. application Ser. No. 10/251,681, filed Sep. 20, 2002; Laser Weldable Flexible Medical Tubings, Films and Assemblies Thereof, U.S. application Ser. No. 10/251,682, filed Sep. 20, 2002; and Laser Weldable Flexible Medical Tubings, Films and Assemblies Thereof, U.S. application Ser. No. 10/251,683, filed Sep. 20, 2002. These systems may employ a laser for heating. One drawback of these systems is that a substantial amount of power is required heat the end portions of the tubing sections. The conventional medical tubing material does not absorb the energy of the electromagnetic radiation well, so considerable energy is required to melt the tubing. Moreover, these methods have still required heating, followed by movement of the tubing sections into engagement. The axially facing surfaces of the end sections are exposed for some considerable time to the surroundings. Moreover, the axially facing surfaces still have to be heated enough so that they do not cool down too much before they are moved into contact with each other.

SUMMARY OF THE INVENTION

A method for connecting together two sections of tubing of the present invention generally comprises the step of placing the two tubing sections in opposed, end-to-end relation so that axially facing surfaces of the tube sections at the ends are free from exposure to the surrounding environment. After this step an electromagnetic beam is directed generally toward the location where the axially facing surfaces are in opposed, end-to-end relation for welding the two sections of tubing together at the location.

In another aspect of the invention, a method of sealing a section of tubing generally comprises placing a portion of the tubing section to be sealed in contact with an energy absorption member. A beam of electromagnetic energy is directed onto the energy absorption member. The energy absorption member is constructed for absorbing energy from the beam. Heat is transferred from the energy absorption member to the tubing section portion by contact therewith to melt the tubing section portion.

Other objects and features of the present invention will be in part apparent and in part pointed out hereinafter.

BRIEF DESCRIPTION OF THE DRAWINGS

FIG. 3 is the view of FIG. 2 but illustrating welding shut the end of the other of the tubing sections;

Corresponding reference characters indicate corresponding parts throughout the several views of the drawings.

DESCRIPTION OF THE PREFERRED EMBODIMENTS

Figure 1:
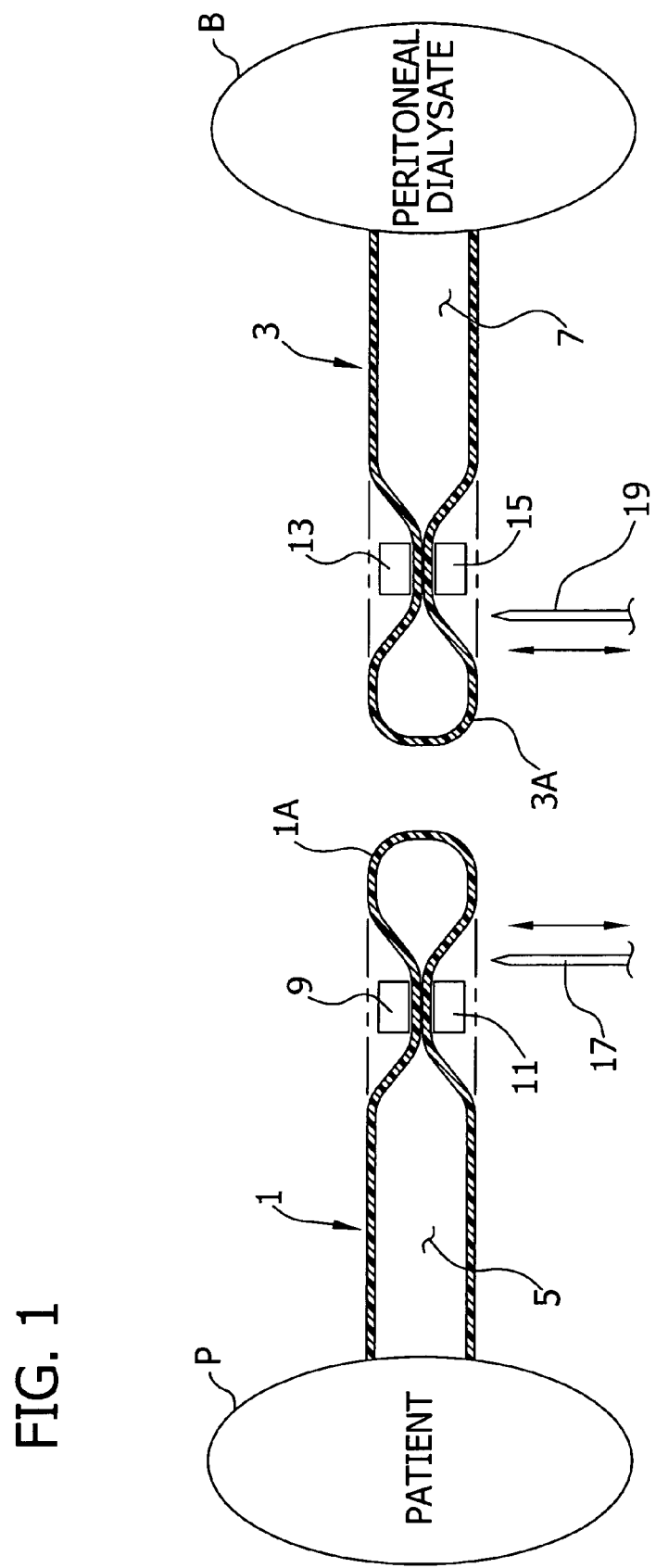
FIG. 1 is a schematic, fragmentary longitudinal section of two tubing sections clamped off generally adjacent ends thereof.
Figure 6:
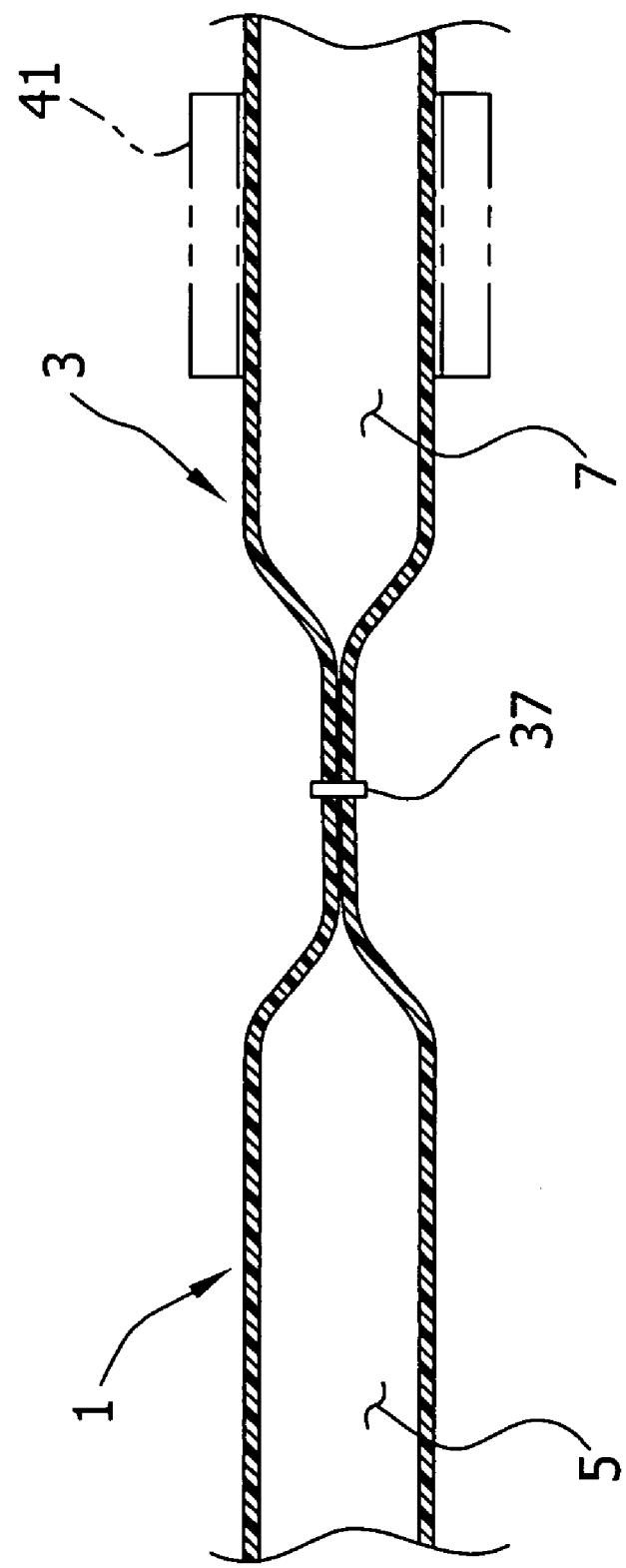
FIG. 6 is the two tubing sections after welding.
Figure 7:
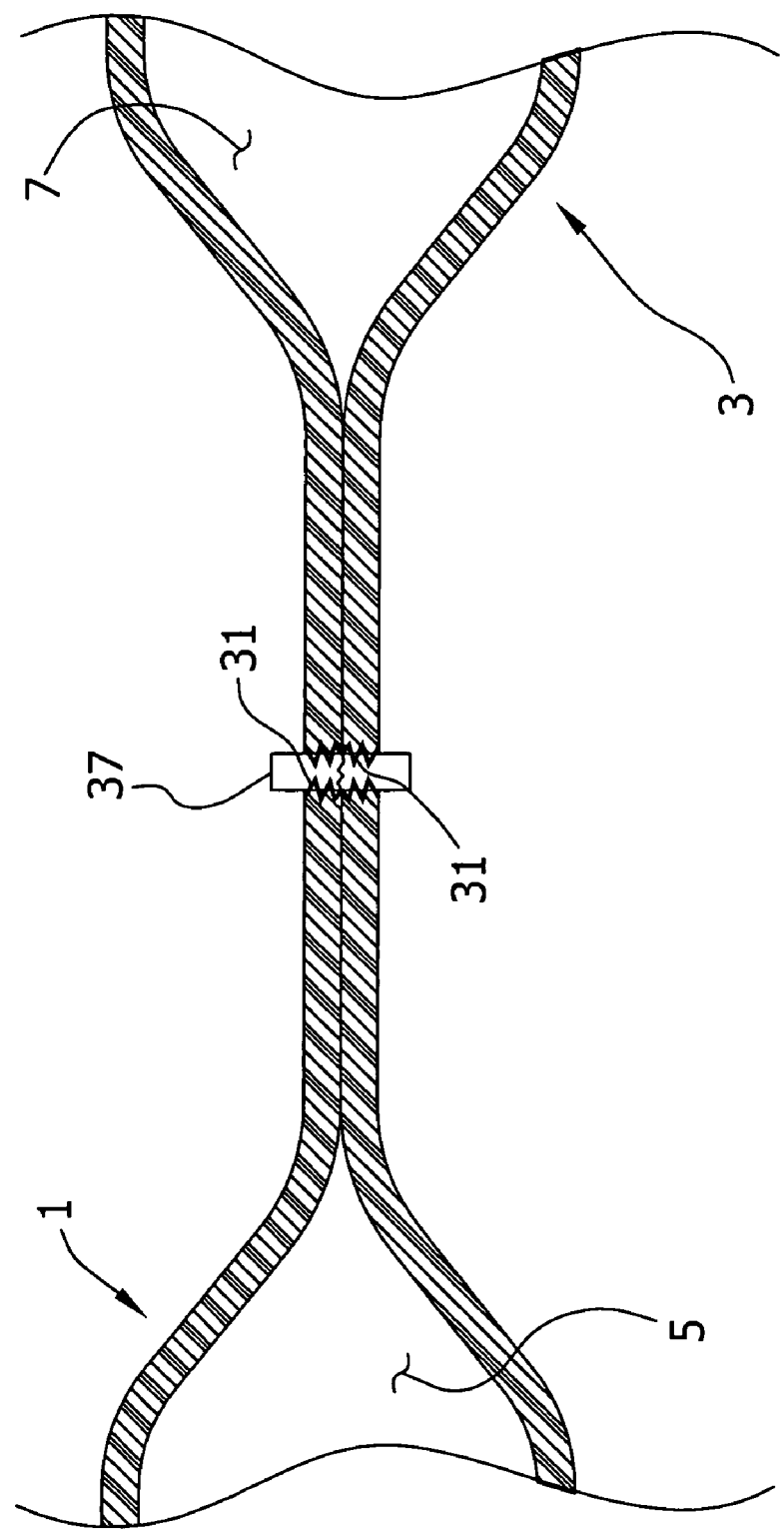
FIG. 7 is an enlarged, fragmentary view of the tubing sections of FIG. 6 at a joint of the tubing sections.
Figure 8:
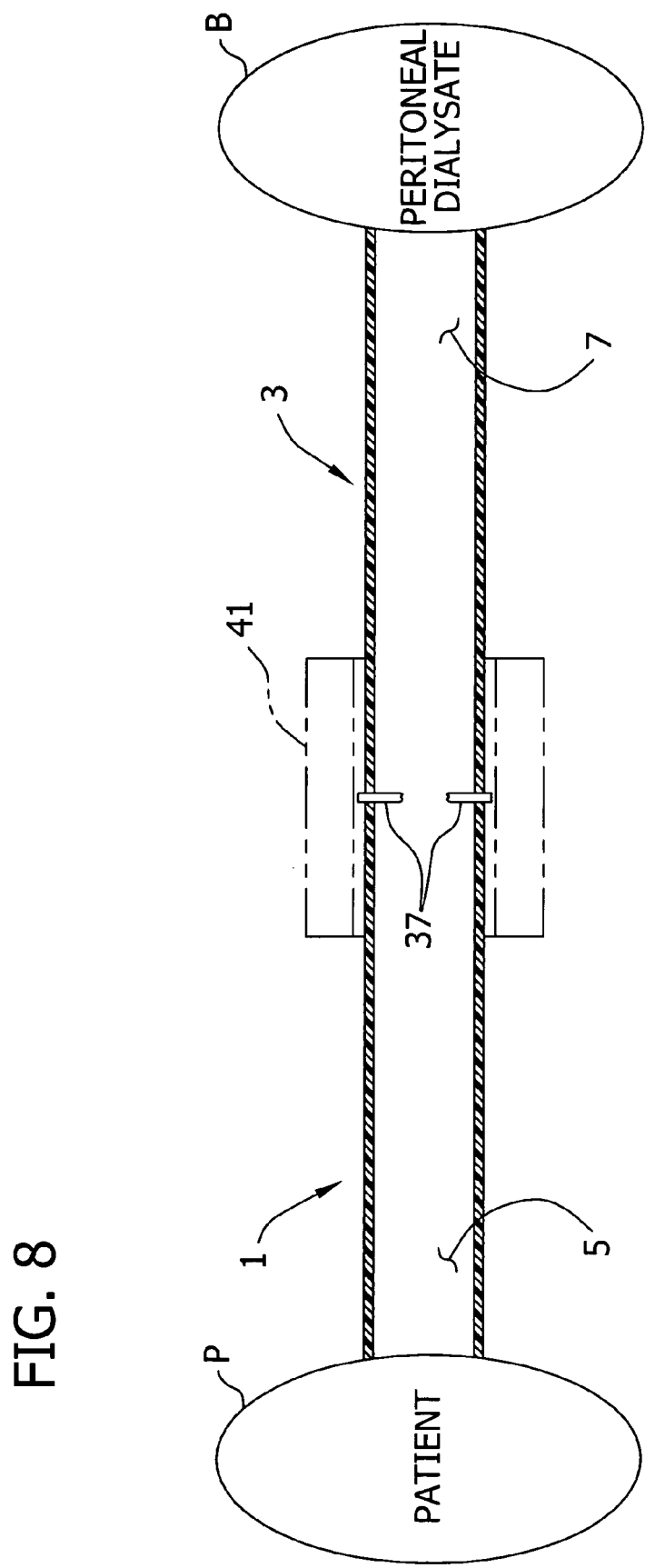
FIG. 8 is the tubing sections of FIG. 6 with the tubing sections reopened at the joint.

Referring now to the drawings and in particular to FIGS. 1-8, a method and apparatus for connecting two tubing sections are schematically illustrated. The tubing sections (designated generally at 1 and 3, respectively) are shown as having closed end portions 1A and 3A. The present invention has particular, although not exclusive, application where it is important to keep the interior passages (5 and 7, respectively) of the tubing sections 1, 3 sterile or substantially sterile while connection the tubing sections together. The medical uses described in the Background of the Invention are exemplary. In that regard, FIGS. 1 and 8 schematically show the tubing section 1 connected to a patient P and tubing section 3 connected to a bag B of peritoneal dialysate. Typically, the tubing sections 1, 3 are flexible but are not required to be so to fall within the scope of the present invention. The material of the tubing sections should be capable of fusing when heated. Conventional medical tubing materials, such as thermoplastics, KRATON polypropylene blends and PVC are suitable. Usually both tubing sections 1, 3 are made of the same material. Otherwise, it is likely necessary to provide some special integrating material to join the two sections together.

Figure 4A:
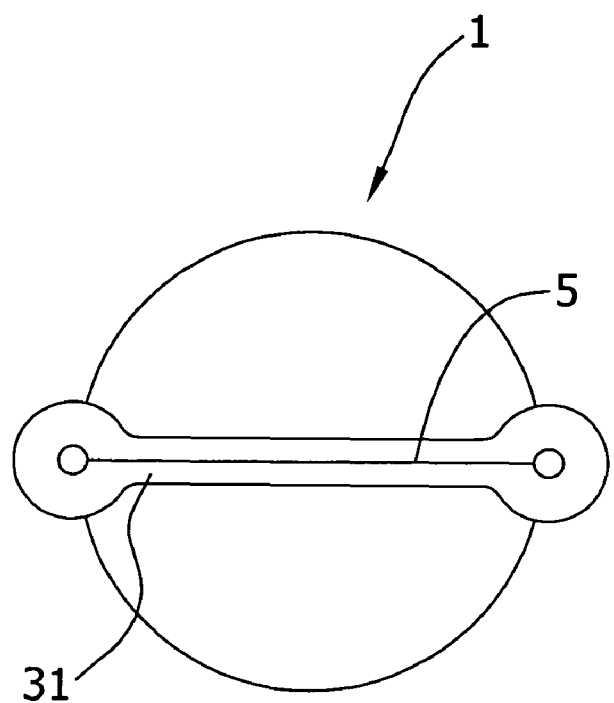
FIG. 4A is an end elevation of one of the tubing sections as clamped.

FIG. 1 illustrates the two tubing sections 1, 3 received in a cutting and welding apparatus, components of which are schematically illustrated along with the tubing sections in FIGS. 1-3, 5 and 6. Clamps acting on the tubing section 1 are designated by reference numerals 9 and 11 and clamps acting on the tubing section 3 are designated by reference numerals 13 and 15. Respective pairs of clamps (9, 11 and 13, 15) have come together in FIG. 1 against the tubing sections 1, 3 to collapse each tubing section near the closed end portions 1A, 3A of the sections. In the regions collapsed, the interior passages 5, 7 are completely or nearly completely shut (see, FIG. 4A showing tubing section 1). The collapsed region is generally that region of the tubing section (1 or 3) which is engaged by the clamps (9, 11 or 13, 15) and adjacent regions where the interior passage (5 or 7) is completely or almost completely collapsed (i.e., so that portions of the tubing section which oppose each other in the interior passages are brought into engagement). The uncollapsed configuration of the collapsed tubing section regions is illustrated in phantom in the FIG. 1. Blades 17 and 19 shown below respective ones of the tubing sections 1, 3, are located axially outward from the location where the clamps (9, 11 or 13, 15) engage that tubing section. The blades 17, 19 are capable of reciprocating as illustrated by the double arrows for moving upward to sever the closed end portions 1A, 3A of the tubing sections from the remainder of the tubing section, and then withdrawing back below the tubing sections 1, 3. The blades 17, 19 can be mounted on cylinders, linear actuators, levers or the like (not shown) for producing the reciprocating motion. It is envisioned that the end portions 1A, 3A of the tubing sections 1, 3 could be severed in other ways (not shown). The end portions 1A, 3A could be collapsed and internally sealed where collapsed. Each end portion could be cut through by a blade or pulled to break off from the remainder of the tubing section where the seal was formed.

Figure 2:
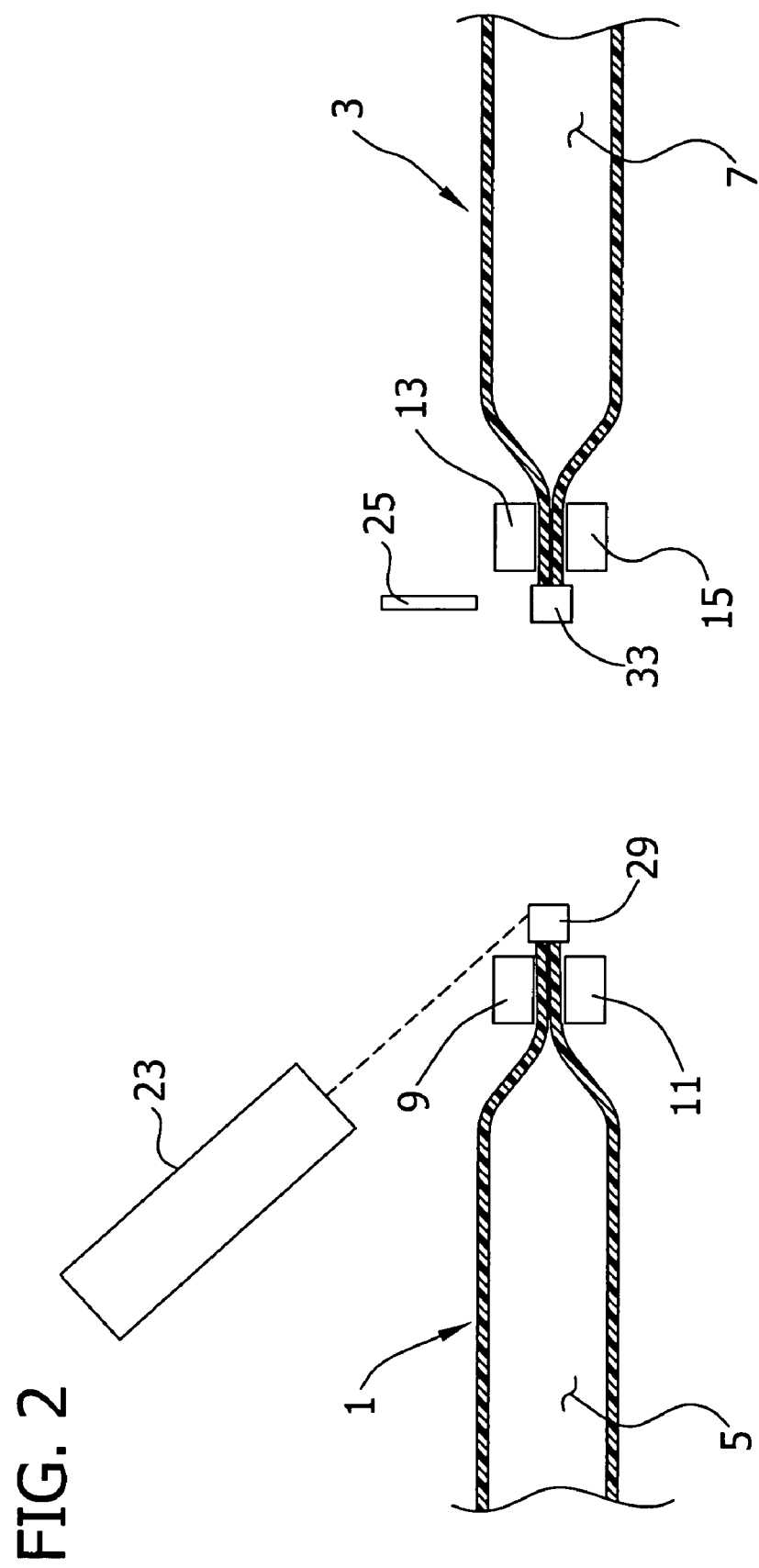
FIG. 2 is a view similar to FIG. 1 but showing the tubing sections after end portions have been cut away, and illustrating welding shut the end of one of the tubing sections.

The same two tubing sections 1, 3 are illustrated in FIG. 2 after their end portions 1A, 3A have been cut away by the blades 17, 19. An end elevation of one clamped, cut tubing section 1 is shown in FIG. 4A. The clamps 13, 15 are not illustrated in FIG. 4A. It is noted that there is some gapping at the opposite sides of the interior passage 5 which is collapsed (and appears substantially as a transverse slit in FIG. 4A). The presence of gaps indicates that the interior passage 5 is not isolated from the surrounding environment. Therefore, the end of the tubing section 1 will be sealed to fully isolate the interior passage 5.

Figure 4B:
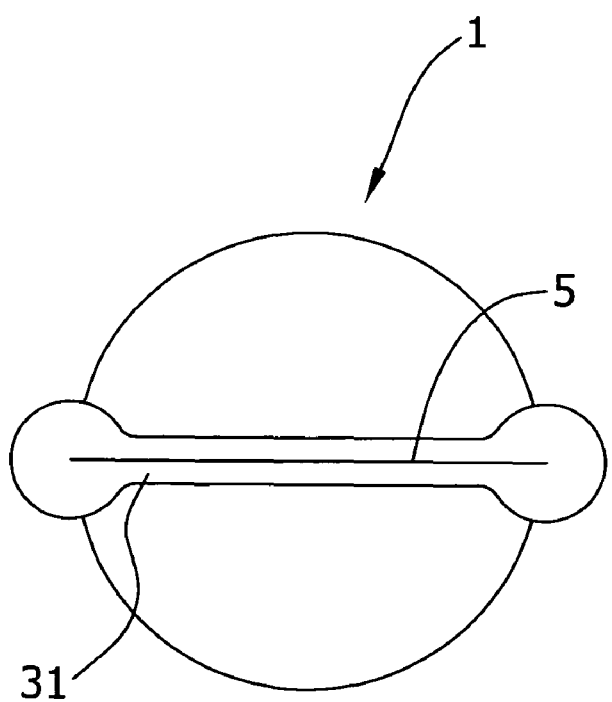
FIG. 4B is an end elevation of one of the tubing sections as clamped and sealed.

Some additional components of the apparatus used to connect the tubing sections 1, 3 are shown in FIG. 2. A photodiode laser 23 supported by the apparatus is positioned above the tubing sections 1, 3 and emits a beam at an angle of about 45° to the aligned longitudinal axes of the tubing sections 1, 3. It is believed that the laser 23 can be oriented so that its beam makes an angle from 15° to 80° and still operate effectively. A mirror 25 will be used as described hereinafter. The laser 23 may broadly be considered a source of an electromagnetic beam. The end of the tubing section 1 on the left in FIG. 2 is positioned so that the laser beam impinges upon a first weld block 29 immediately adjacent and engaging an axially facing surface 31 (see, FIG. 4A) of the end of the tubing section 1. The tubing sections 1, 3 are both essentially transparent to the radiation emitted from the laser 23 used in this embodiment, and would not be heated (or would be heated only very slowly) by the photodiode laser. The first weld block 29 includes a material which absorbs the energy of the laser beam, becoming hot. For example, the first weld block 29 may be made of black polytetraflouroethylene or black glass, which absorb energy but are poor heat conductors. The heat is transferred by conduction from the first weld block 29 to the axially facing surface 31 of the tubing section 1 in contact with the first weld block, melting a portion of the section and sealing it shut. An end elevation of the clamped and sealed tubing section 1 is shown in FIG. 4B.

Fixtures (not shown) of the apparatus holding the tubing sections 1, 3 and mirror 25 shift so that the mirror is brought into the path of the laser beam from the laser 23 (FIG. 3). It is contemplated that the laser 23 could be moved while the fixtures and tubing sections 1, 3 held therein remain stationary. The mirror 25 redirects the beam onto a second weld block 33 engaging an axially facing end surface of the right tubing section 3 (not shown, but like the surface 31 of tubing section 1). The second weld block 33 is made of the same material as the first weld block 29 and transfers heat by conduction to the axially facing surface of the tubing section 3 in contact with the second weld block to melt and seal the end of the tubing section. The first and second weld blocks 29, 33 may be broadly considered as "energy absorption members."

The seals achieved at the ends of the tubing sections 1, 3 isolate the interior passages 5, 7 of the tubing sections from contamination from the surrounding environment, and also prevent any liquid which might be present in one or both of the tubing sections from flowing out of the tubing section. The seals are made so that they may be relatively easily broken after the tubing sections 1, 3 are joined together, as will be described hereinafter. It will be understood that the seals may be formed in any suitable manner. For instance, a second laser (not shown) may be provided so that both tubing sections 1, 3 could be welded shut substantially simultaneously. Instead of a second laser, a portion of the beam from a single laser could be transmitted by a light pipe or mirrors (not shown) to the other tubing section, allowing both tubing sections to be welded shut and the same time. If a sufficiently powerful laser is used, the weld blocks 29, 33 would not be required.

Moreover, instead of the laser 23, the blades 17, 19 may be heated so that the ends of the tubing sections 1, 3 are sealed at the same time they are cut through by the blades. The heating could occur by resistance heating, or by having the beam of the laser 23 impinge upon the blade (17 or 19) while the blade engages the axially facing surface 31 of the end of the tubing section (1 or 3). The first and second weld blocks 29, 33 could be heated by conventional resistance heating. A sonic or RF welder (not shown) could also be used, which would not require the weld blocks 29, 33. However by using the laser 23, the apparatus requires only a single energy source for all of the sealing/joining functions performed by the apparatus. It is also envisioned that an end segment of each tubing section could be fused shut (e.g., clamped and sealed using the weld blocks). Then the blades 17, 19 could be activated to cut through the seals. The end portion (1A or 3A) of the tubing section (1 or 3) would still be severed, but enough of the seal would remain so that the end of the tubing section would remain sealed and closed after the end portion was cut away.

Figure 5:
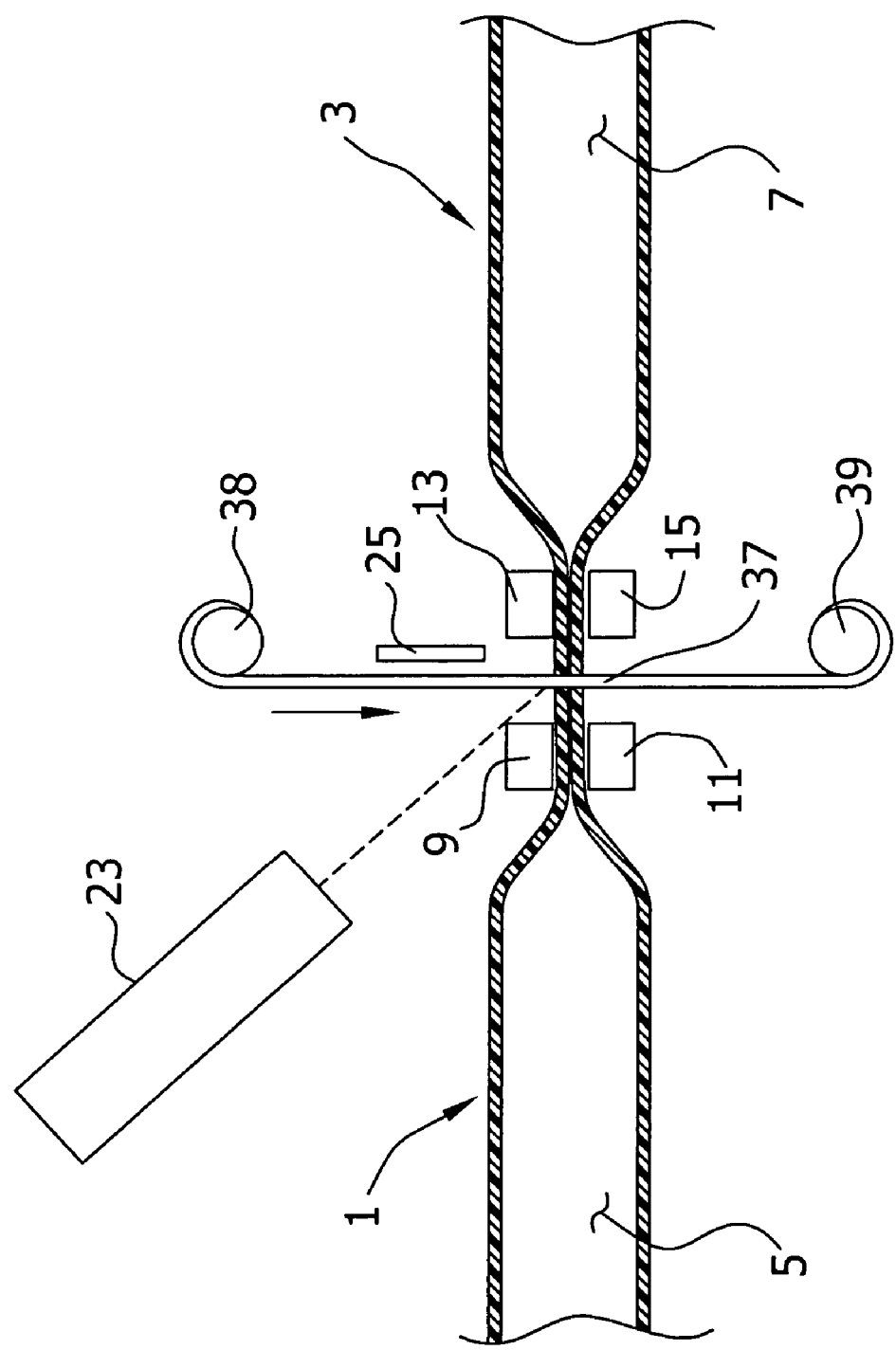
FIG. 5 is a schematic of the two tubing sections of FIG. 3 being welded together with a laser.

The first and second weld blocks 29, 33 are removed from engagement with the axially facing surfaces 31 of the ends of the tubing sections 1, 3 and out of the way of the tubing sections. A segment of film 37 (broadly, "a sheet of material" and "an energy absorption member") is positioned between the opposed axially facing surfaces 31 of the tubing sections 1, 3 and the fixtures are moved to bring the axially facing end surfaces 31 into engagement with opposite sides of the film, as shown in FIG. 5. The film 37 is made of a material which is compatible with the material of the tubing sections 1, 3. For instance, if the tubing sections include a polypropylene component, so will the film. If the tubing sections are made of PVC, then the film also includes PVC or a compatible polymer. The thickness of the film 37 is preferably less than or equal to about 200 microns, and more preferably in the range of about 10 to 100 microns. The thickness of the film 37 in proportion to the size of the tubing sections 1, 3 has been greatly exaggerated in the drawings so that the film can be seen when viewed edge-on as in FIG. 5. Unlike the tubing sections 1, 3, the film 37 contains a dye or pigment, or is otherwise formed so that it absorbs the energy of the laser 23 for use in connecting the tubing sections, as will be described hereinafter. The film 37 allows the use of a highly efficient photodiode laser 23. These lasers require low power to operate and are easily miniaturized. Moreover, the beam of a photodiode laser 23 is readily guided by optical fiber or light pipe (should that be desired). It is to be understood that more than one laser could be used to fuse the tube sections together. The second laser (not shown) could be directed against the film on the side of the film opposite the side impinged by the laser 23.

The film 37 extends in a web between a supply roll 38 and a take-up roll 39 through a position between the axially facing end surfaces 31 of the tubing sections 1, 3, as shown in FIG. 5. The film 37 is preferably maintained in an aseptic condition prior to use, so at least the supply roll 38 may be housed in a sterile cassette (not shown). A piece of film 37 can be separated from the roll (e.g., by the laser 23) for incorporation into the tubing sections 1, 3 for connecting the sections as will be described hereinafter. The piece is taken from one longitudinal edge of the film 37 so that the web is not cut through its width. Thus, the take-up roll 39 can be used to index the film 37 for use in connecting the next two tubing sections together. In another version (not shown), numerous pieces of film can be attached to a continuous carrier which extends between the rolls. The film piece is used to connect the tubing sections 1, 3, but the carrier remains intact for use in indexing the next film piece into position. Other arrangements for delivering the film 37 may be employed without departing from the scope of the present invention.

Referring to FIG. 5, the laser 23 is energized to direct its beam against the film 37. The beam may have a shape in cross section which is similar to the cross section of the flattened tube sections 1, 3 where they engage the film 37. In one embodiment, the beam impinges upon the film 37 everywhere the film engages the axially facing end surfaces 31 of the tubing sections 1, 3. However, the beam may not impinge upon the film 37 in all locations where the film engages the end surfaces 31 of the tubing sections 1, 3 without departing from the scope of the present invention. The film 37 rapidly becomes heated and transfers heat by conduction to the axially facing surfaces 31 of the ends of the tubing sections 1, 3. The heat transferred is such that the film 37 and axially facing end surfaces 31 fuse together (i.e., diffuse into one another), forming a robust connection. The tensile strength of the connected tubing sections 1, 3 including the joint where they are connected together is about 95% of the tensile strength of the original tubing sections. It is necessary to heat only a very small area and volume to a temperature which melts ends of the tubing sections 1, 3, keeping power demands on the laser 23 to a minimum.

Figure 7A:
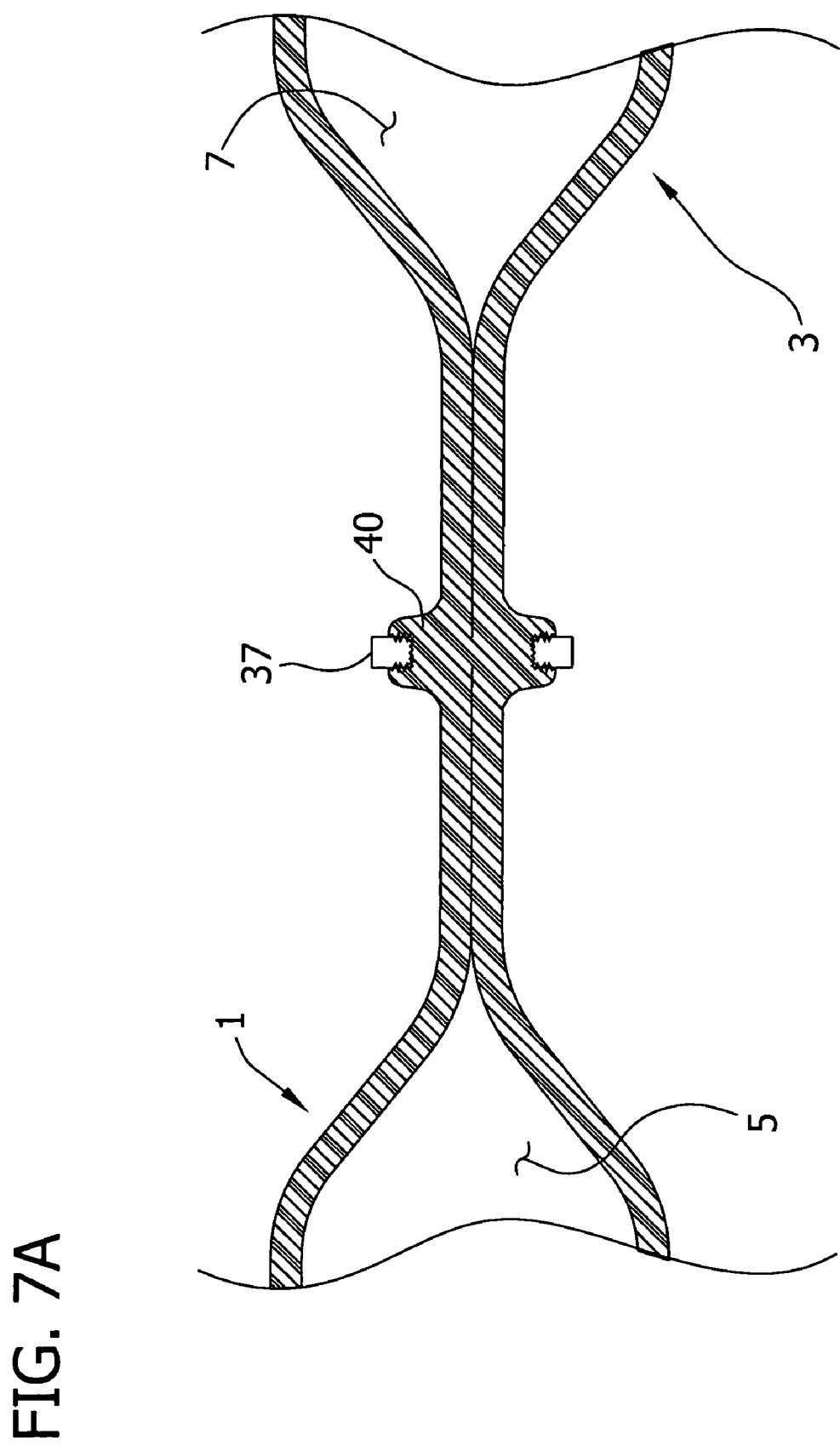
FIG. 7A is the enlarged, fragmentary view of FIG. 7, but showing the tubing sections pushed together to displace material at the joint.

In a modified version of the process shown in FIG. 7A, the laser 23 is turned on for a few seconds, substantially as described above for FIG. 5 so that the axially facing surfaces of the tubing sections 1, 3 become hot and fluid. In the FIG. 7A process, the laser 23 is then turned off and the fixtures holding the tubing sections 1, 3 are moved so that the tubing sections advance toward each other a small distance (e.g., about 0.5 mm). This movement presses the axially facing end surfaces 31 of the tubing sections 1, 3 against each other, and causes the molten material of the tubing sections to flow radially outwardly, producing a bulge of tubing section material around the joint. This flow also is believed to split the film apart, as shown in FIG. 7A. It has been found that it is easier to break the seals holding the tubing sections 1, 3 in a collapsed condition for reopening the interior passages 5, 7 after the tubing sections are joined together when this additional step is carried out. It is to be understood that the step of moving the tubing sections 1, 3 toward each other may be performed while the laser 23 is still on, or may be omitted without departing from the scope of the present invention.

As shown in FIG. 6, the tubing sections 1, 3 are now joined together, but remain in a collapsed condition. The joined tubing sections 1, 3 are shown separate from the connecting apparatus. An enlarged view of the joint in FIG. 7 illustrates how the materials of the film 37 and tubing sections 1, 3 have diffused into each other. It is believed that the film 37 will split open where it is not in contact with the axially facing surfaces 31 of the tubing sections 1, 3 during the connection step when the laser beam is directed onto the film. Opening the collapsed regions of the connected tubing sections 1, 3 can be accomplished by squeezing the tubing sections in the collapsed region. More specifically, the force of squeezing would be applied on opposite sides of the collapsed region in a plane generally perpendicular to the plane of the page of FIG. 6 and extending generally along the longitudinal axis of the joined tubing sections 1, 3. The seals of the ends of the tubing sections formed prior to joining the tubing sections 1, 3 together are readily broken, allowing the tubing sections to assume the configuration shown in FIG. 8. Again, the length and thickness of the bits of film 37 remaining have been greatly exaggerated so that they can be seen in the several views of the drawings.

In some instances it is desirable to keep the joined tubing sections in a sealed and collapsed condition until ready for use. For example, one may wish not to mix flowable products contained in two bags connected by the tubing sections 1, 3 until it is time to use the products. In that event, the joined tubing sections 1, 3 would remain collapsed and sealed until time for use. Opening the tubing section 1, 3 so that the interior passage 5, 7 form one continuous passage can be carried out as above. In addition, a clamp or sleeve could be provided at the joint to make certain the tubing sections 1, 3 remain sealed until needed.

The tubing sections 1, 3 are now ready for use, carrying product (e.g., blood, dialysate) from one tubing section to the other. Because the tubing sections 1, 3 were closed during the joining process, the interior passages 5, 7 remain sterile and free of foreign materials (e.g., material from the exterior of the tubing sections). Moreover, the heat of the laser 23 has a sterilizing effect in the region of the connection. Thus, areas (e.g., the film 37 and axially facing surfaces 31) which are exposed even for brief periods to the surrounding environment are protected further from contamination. Tests conducted by intentionally contaminating each of the opposite surfaces of the film 37 with $10^6$ spores of bacteria (*Bacillus subtilis*) have demonstrated that the tubing sections 1, 3 can remain sterile after being joined together with the contaminated film by control of the power of the laser 23.

FIGS. 6 and 8 also illustrate a slightly different version of the present invention in which a tubular sleeve 41 (shown in phantom) is slidably mounted on one of the tubing sections 1, 3. The sleeve 41 is positioned off to the side of the location where the connection between the tubing sections 1, 3 is being made (FIG. 6). However once the connection is complete, the sleeve 41 may slide to a position in registration with the joint formed (FIG. 8). The sleeve 41 conforms closely to the open shape of the tubing sections 1, 3 and acts to hold the interior passages 5, 7 of the tubing sections 1, 3 open in use at the point of connection. In some instances, the connected tubing sections 1, 3 may have a tendency to kink and close off the interior passages 5, 7 at the joint during use of the tubing sections. The sleeve 41 guards against this occurrence. Other structures for inhibiting kinking may be employed, such as a clam shell sleeve (not shown) which can be opened and completely removed from the tubing sections 1, 3 when not needed.

The joined tubing sections 1, 3 can be separated, such as by a blade of the apparatus or other suitable device (not shown) after use. In many instances, one of the tubing sections (e.g., tubing section 3) is discarded. However, the other tubing section 1 is used to make a second and possibly subsequent connections to other tubing sections (not shown). The discarded tubing section 3 may be, for example, a tubing section connected to the bag B of dialysate in a peritoneal dialysis procedure (FIG. 8). The reused tubing section 1 may be connected to a catheter (not shown) implanted in a patient P. In that event, the tubing sections 1, 3 are separated by cutting through the tubing section 3 to be discarded to one side of the joint. The next joint is formed at a location spaced closely with the first joint and within the reused tubing section 1. In this way the reused tubing section 1 is not used up as rapidly.

The step of sealing each of the tubing sections 1, 3 closed at the ends by fusion (see discussion in reference to FIGS. 2 and 3) can be eliminated in one version of the present invention. If clamps 45, 47 and 49, 51 collapsing tubing sections (generally indicated at 53 and 55, respectively in FIG. 9) are placed close to the ends of the tubing sections, the clamps can hold the tubing sections in an essentially sealed condition (i.e., the gaps seen at the ends of the interior passage 5 shown in FIG. 4A are substantially eliminated). For example, with tubing sections 53, 55 having wall thicknesses of about 0.6-0.7 mm, the edges of the clamps 45, 47, 49, 51 would need to be located about 0.3 mm or less from the axially facing end surface of the tubing section (not shown in FIG. 9). In contrast, for the method described with reference to FIGS. 1-8, the clamps 9, 11, 13, 15 are set back about 0.4 mm or slightly farther from the axially facing surfaces 31 of the tubing sections 1, 3. Increasing the angle of the beam from the laser 23 to about 70° allows the clamps 9, 11, 13, 15 to be located closer to the axially facing end surfaces of the tubing section 1, 3 without requiring any of the clamps to be transparent to the laser beam. Other arrangements of the laser 23 and clamps 9, 11, 13, 15 are possible without departing from the scope of the present invention.

Figure 9:
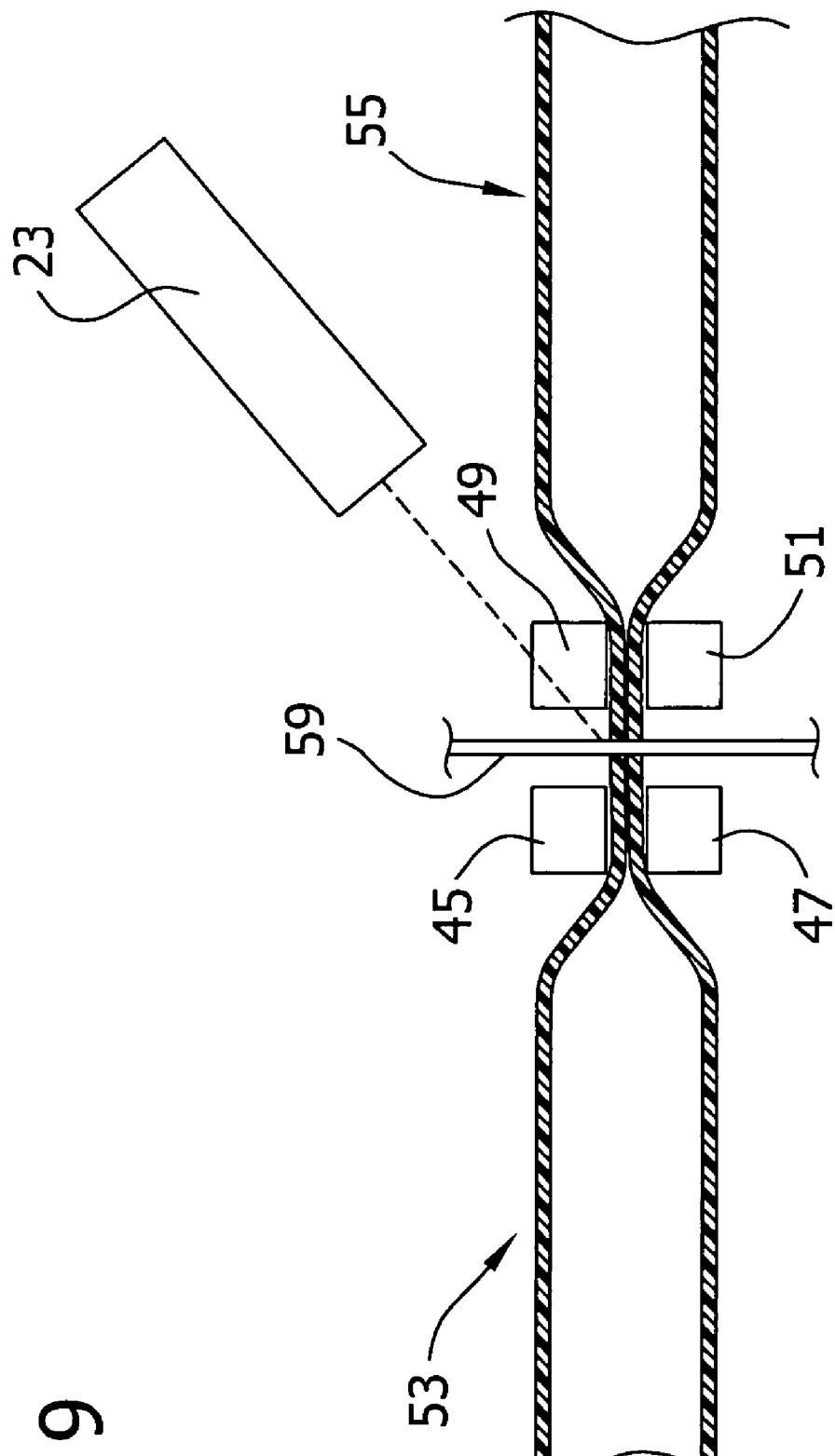
FIG. 9 is a schematic, fragmentary longitudinal section of the tubing sections showing a different configuration for welding.

If the tubing sections 53, 55 are clamped close to their ends, it will be necessary for one or both of the clamps 45, 49 on the top to be transparent to the laser beam from the laser 23 so that the laser beam can access film 59 disposed between the tubing sections 53, 55 in the connection step, as shown in FIG. 9. It will be understood that for the process of FIG. 9, the tubing sections 53, 55 will be clamped and the end portions cut off very close to the clamps 45, 47, 49, 51 (e.g., within 0.3 mm). The sealing illustrated in FIGS. 2 and 3 will not be carried out.

Figure 10:
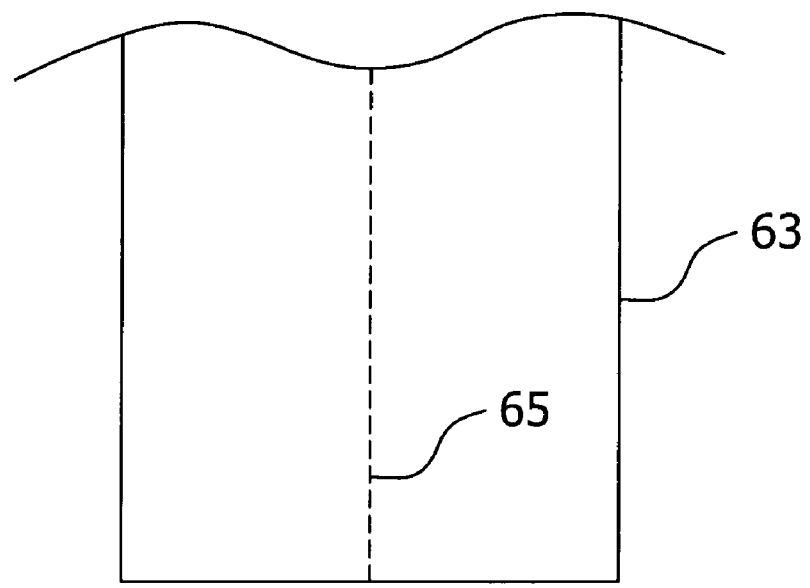
FIG. 10 is a fragmentary elevation of film used for welding the tubing sections together.
Figure 11:
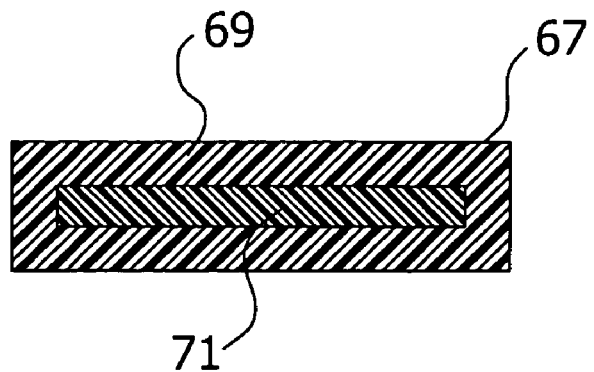
FIG. 11 is a cross section of another kind of film used for welding the tubing sections together.

It is believed that the film (37 or 59) will separate in the middle when the laser 23 acts on the film so that the film will not obstruct reopening of the interior passages formed by the connected tubing sections (1 and 3, 53 and 55). However, film can be constructed to facilitate tearing in the "middle" of the film (i.e., the part of the film not in engagement with an axially facing surfaces 31 of the tubing sections 1, 3). One example is film 63 shown in FIG. 10. We will describe the use of the film 63 hereinafter in relation to the tubing sections 1, 3. Here the film 63 has perforations 65 generally down its middle. The perforations 65 facilitate tearing when the tubing sections 1 and 3 are squeezed to reopen their interior passages 5, 7. Another version of film 67 shown in FIG. 11 co-extrudes an electromagnetic radiation absorbing material 69 together with a different material 71 which does not absorb the laser beam energy. This construction weakens the central part of the film 67 so that it can be more easily torn. By holding the film 67 taut when the laser is energized, the film is substantially instantaneously cut around the outer diameter of the tubing sections 1, 3, separating a piece of the film from the remainder of the roll.

Instead of positioning a web of pigmented film between tubing sections (e.g., as shown in FIG. 5), individual pieces could be applied to one or both of the tubing sections (not shown). More specifically, after a tubing section is collapsed and welded in the collapsed position, a piece of film is attached as by welding to the axially facing end surface of the collapsed end of the tubing section. The tubing section can be brought into engagement with another tubing section (substantially the same as shown in FIG. 5), and the sections welded together with a laser. A variation of this process (not shown) involves attaching another piece of film on the axially facing surface of the other tubing section before the tubing sections are brought into engagement. Still a further variant (not shown) is to attach a piece of film over the open end of one tubing section. The film is brought into engagement with the closed end of another tubing section. The laser is used to fuse the two tubing sections together, and to rupture the film of the one tubing section and closed end of the other tubing section for opening the interior passaged between the two sections.

Figure 12:
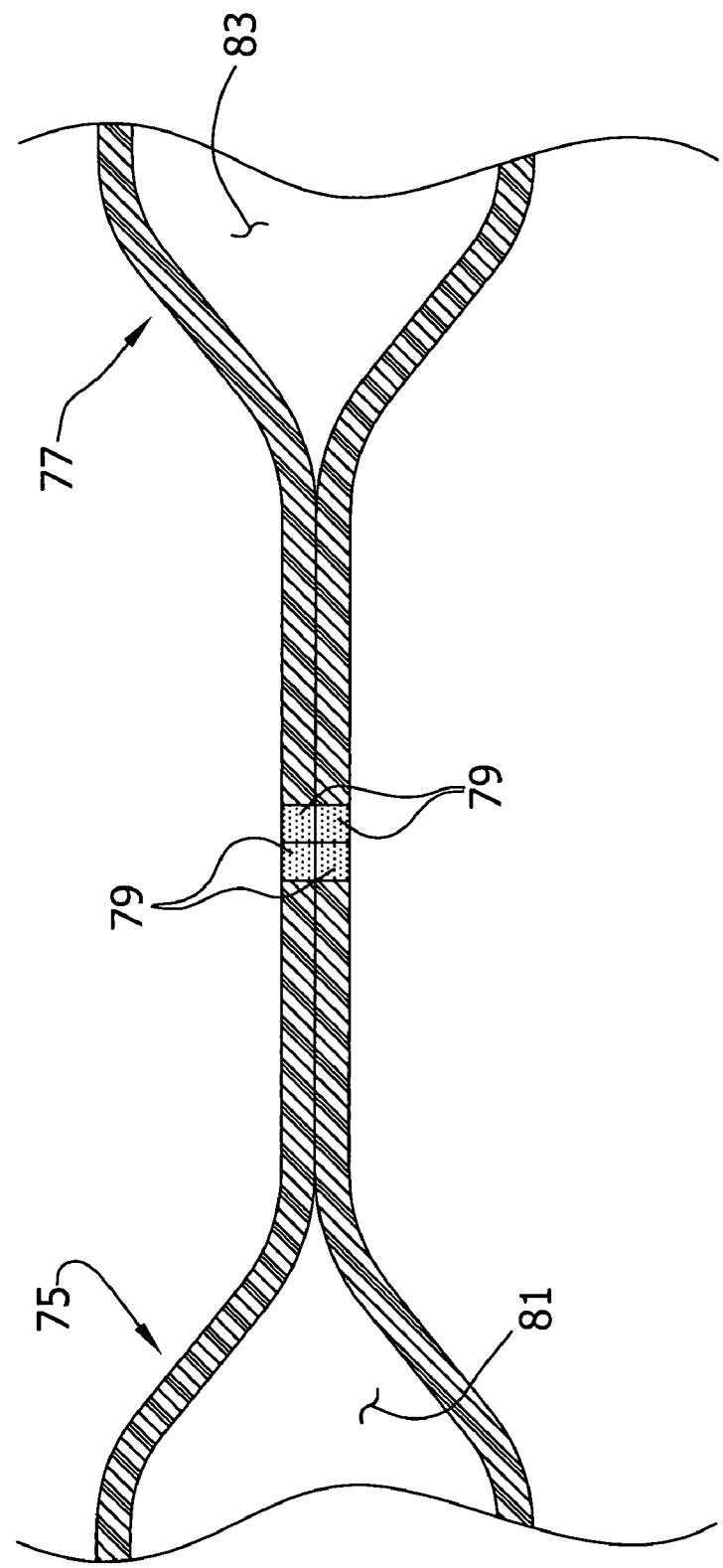
FIG. 12 is a schematic, longitudinal section of two tubing sections which have had a dye applied to the ends prior to welding.

It also is possible to replace the film (37, 59, 63 or 67) by applying a dye or some other coloring substance directly to the axially facing surfaces (not shown, but like axially facing surface 31 of FIGS. 4A and 4B) of the opposed ends of tubing sections indicated generally at 75 and 77 (FIG. 12). It is to be understood that the dye may be applied to only one of the two tubing sections. For instance, the dye could be applied by an ink jet, an ink pad or a marker (not shown). The dye could also be applied from a film onto the axially facing end surface of the tubing section (75 or 77). In that case, a hot die can be activated to press the film against the axially facing surface so that dye carried by the film is transferred onto the axially facing surface of the tubing section (75 or 77). Abutting tubing sections 75, 77 having ends colored with a dye 79 are shown in FIG. 12. The connecting apparatus would have components (not shown) for applying the dye 79 to the axially facing surfaces of the tubing section ends. The laser (not shown) could then be directed onto the ends of the tubing sections 75, 77. The dye 79 causes the material of the tubing sections 75, 77 in the regions colored to absorb the laser energy and heat up enough to fuse the tubing sections together. The axially facing surfaces of the ends of the tubing sections 75, 77 can be brought into engagement first before the laser is activated to fuse the tubing sections together, limiting the exposure of the axially facing surfaces of the tubing sections to the surrounding environment. Interior passages 81, 83 of the joined tubing sections 75, 77 could be reopened by squeezing as described previously.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

Moreover, the use of "above" and "below" and variations of these terms is made for convenience, but does not require any particular orientation of the components.

The invention claimed is:

1. A method of connecting tubing sections comprising:
   for each of the tubing sections:
   clamping at least a portion of the tubing section such that a collapsed portion of the tubing section extends past the clamped portion;
   covering an end of the tubing section with an energy absorption member, the energy absorption member formed of a material that absorbs energy from an electromagnetic beam;
   directing the electromagnetic beam onto the energy absorption member;
   transferring heat from the energy absorption member to the collapsed tubing section portion by contact therewith to melt and seal the collapsed tubing section portion in its collapsed configuration; and
   removing the energy absorption member;
   placing the tubing sections in opposed, end-to-end relation;
   positioning a separate sheet of material between axially facing surfaces at the ends of the tubing sections, the sheet being formed of a material which absorbs energy of the electromagnetic beam;
   bringing the respective axially facing surfaces of the tubing sections into engagement with the sheet; and
   directing the electromagnetic beam onto the sheet for welding the sections of tubing together.

2. A method as set forth in claim 1 wherein the energy absorption member has low thermal conductivity.

3. A method as set forth in claim 2 wherein the energy absorption member comprises a block.

4. A method as set forth in claim 3 wherein the block is made of one of polytetrafluoroethylene and glass.

5. A method as set forth in claim 1 wherein the energy absorption member comprises a film.

6. A method as set forth in claim 1, wherein the collapsed portion of the tubing section is an end of the tubing section.

7. The method of claim 1, which includes extending the sheet of material between a supply roll and a take-up roll.

\* \* \* \* \*